United States Patent [19]

Farkas et al.

[11] Patent Number: 5,683,359
[45] Date of Patent: Nov. 4, 1997

[54] ARTHROSCOPIC SURGICAL INSTRUMENTS HAVING SUCTION CAPABILITY

[75] Inventors: Laszlo Farkas, Hialeah; Kevin F. Hahnen, Ft. Lauderdale; Boris Kesler, Hialeah, all of Fla.

[73] Assignee: Symbiosis Corporation, Miami, Fla.

[21] Appl. No.: 515,937

[22] Filed: Aug. 16, 1995

Related U.S. Application Data

[63] Continuation of Ser. No. 180,434, Jan. 12, 1994, abandoned, which is a continuation-in-part of Ser. No. 978,249, Nov. 18, 1992, Pat. No. 5,395,375, and a continuation-in-part of Ser. No. 74,790, Jun. 10, 1993, Pat. No. 5,395,364.

[51] Int. Cl.⁶ .................................... A61B 17/32
[52] U.S. Cl. .................. 604/22; 606/83; 606/170; 606/184
[58] Field of Search .................. 606/205–207, 606/79, 83, 184, 170; 128/751, 752; 604/22

[56] References Cited

U.S. PATENT DOCUMENTS

| | | | |
|---|---|---|---|
| 3,173,414 | 3/1965 | Guillant | 128/752 |
| 3,964,468 | 6/1976 | Schulz | 128/751 |
| 4,522,206 | 6/1985 | Whipple et al. | 128/312 |
| 4,632,110 | 12/1986 | Sanagi | 128/303 |
| 4,644,951 | 2/1987 | Bays | 606/170 |
| 4,646,751 | 3/1987 | Maslanka | 128/751 |
| 4,712,545 | 12/1987 | Honkanen | 128/305 |
| 4,763,668 | 8/1988 | Macek et al. | 128/751 |
| 4,785,825 | 11/1988 | Romaniuk | 128/751 |
| 4,944,093 | 7/1990 | Falk | 30/251 |
| 4,953,559 | 9/1990 | Salerno | 128/751 |
| 4,971,067 | 11/1990 | Bolduc et al. | 128/751 |
| 5,082,000 | 1/1992 | Picha | 128/751 |
| 5,112,346 | 5/1992 | Hiltebrandt | 606/170 |
| 5,125,910 | 6/1992 | Freitas | 604/249 |
| 5,147,292 | 9/1992 | Kullas et al. | 604/34 |
| 5,152,780 | 10/1992 | Honkanen et al. | 606/205 |
| 5,186,714 | 2/1993 | Boudreault | 604/21 |
| 5,195,958 | 3/1993 | Phillips | 604/33 |
| 5,217,460 | 6/1993 | Knoepfler | 606/52 |
| 5,219,357 | 6/1993 | Honkanen et al. | 606/205 |
| 5,336,238 | 8/1994 | Holmes et al. | 606/205 |
| 5,344,428 | 9/1994 | Griffiths | 606/170 X |

FOREIGN PATENT DOCUMENTS

| | | | |
|---|---|---|---|
| 526115 | 2/1993 | European Pat. Off. | 606/205 |
| 4135554 | 5/1992 | Japan | 606/205 |
| 07516 | 5/1992 | WIPO | 128/752 |

Primary Examiner—Michael H. Thaler
Attorney, Agent, or Firm—David P. Gordon

[57] ABSTRACT

An arthroscopic surgical instrument includes a surgical punch end effector assembly, a hollow tube defining a fluid passageway, a push rod extending through the hollow tube, an actuating lever coupled to a proximal end of the push rod, and a fluid coupler extending into the hollow tube and coupling to a vacuum source which applies suction through the fluid passageway. The end effector assembly has movable punch and stationary die end effectors. The stationary die end effector includes separate upper die and lower cup portions which are coupled to the distal end of the hollow tube, and which are fixed together during an assembly procedure. The upper die portion has a groove into which a tongue of the movable end effector is fitted prior to fixing the separate portions of the stationary end effector. When the stationary die end effector is assembled with the movable punch end effector pivoting therein, and the end effectors are in a closed position, a substantially closed cavity or hollow is formed in the end effectors with the cavity having a proximal opening to the tube. Tissue punched by the movable end effector falls into the cavity, and due to the fact that the cavity is substantially closed, the suction extends into the cavity and suctions the tissue out through the fluid passageway.

22 Claims, 5 Drawing Sheets

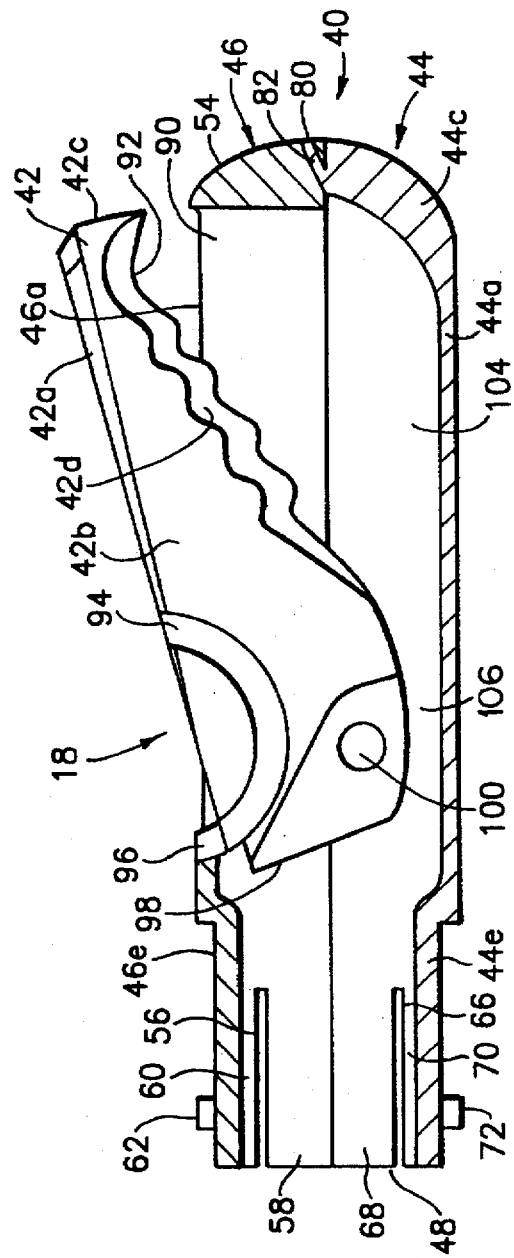

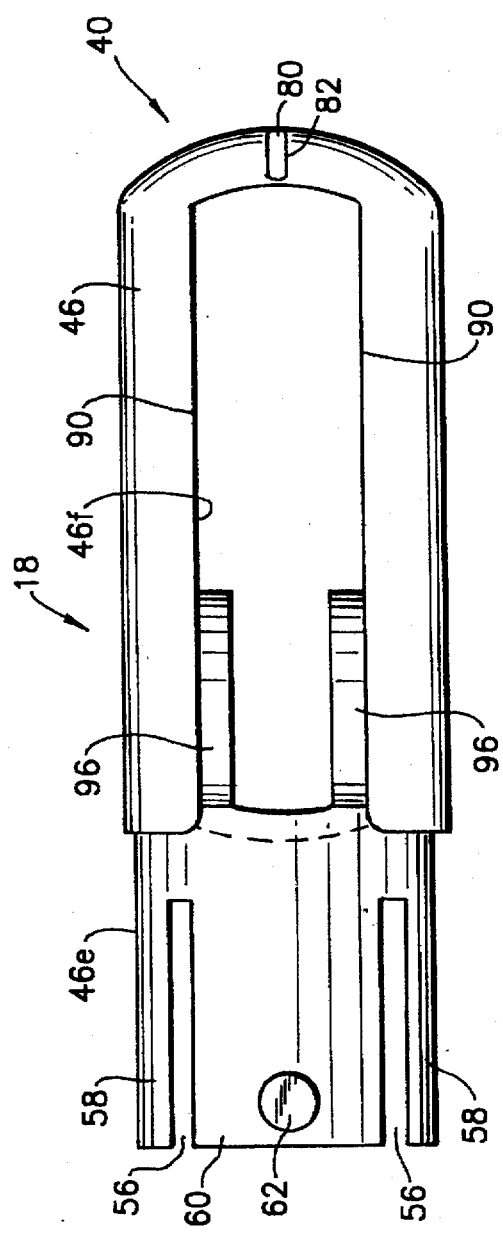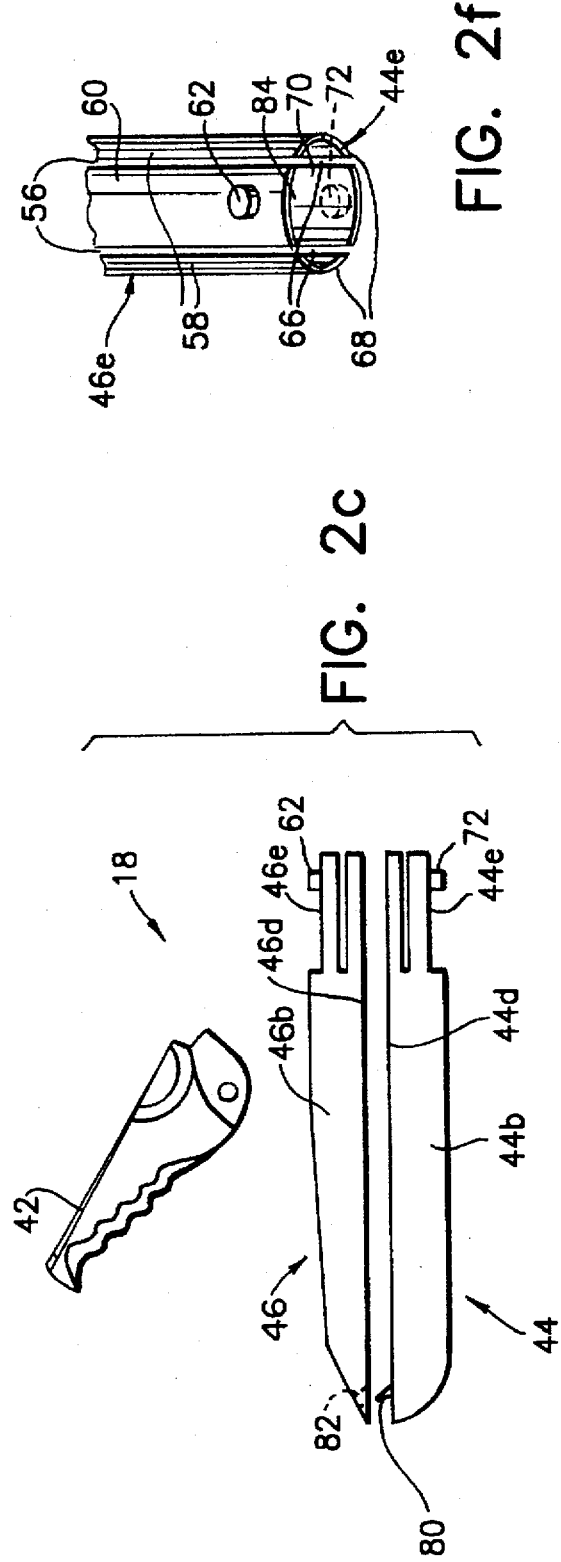

ARTHROSCOPIC SURGICAL INSTRUMENTS HAVING SUCTION CAPABILITY

This application is a continuation of application Ser. No. 08/180,434 filed Jan. 12, 1994, now abandoned which is continuation-in-part of coassigned applications Ser. No. 07/978,249 filed Nov. 18, 1992, and now issued as U.S. Pat. No. 5,395,375, and Ser. No. 08/074,790 filed Jun. 10, 1993, and now issued as U.S. Pat. No. 5,395,364 the complete disclosures of which are hereby incorporated herein by reference in their entirety.

BACKGROUND OF THE INVENTION

1. Field of the Invention

The present invention relates to arthroscopic surgical instruments. In particular the present invention relates to arthroscopic surgical instruments which incorporate a suction capability.

2. State of the Art

Arthroscopic surgical instruments are instruments used in the surgical repair of joints where the joint is not exposed by a large incision. Arthroscopic surgical instruments generally include an actuating handle coupled by a tube and push rod to an end effector assembly. The end effector assembly typically includes a pair of jaws, one of which is rotatably coupled to the other, thereby allowing articulation of one jaw relative to the other. Arthroscopic cutting instruments typically include jaws which achieve a cutting action through a punch and die configuration which severs the tissue from the joint by punching the tissue with a sharp edged jaw through a die. The die typically takes the form of a fixed jaw, while the punch takes the form of a movable jaw which rotates relative to the fixed jaw from an open position to a closed position when cutting.

Arthroscopic surgery is performed on joints of the body to remove damaged cartilage, bone tissue, and spurs, and to repair ligament damage. During the arthroscopic surgical procedure, small incisions are made around the joint, and a cutting tool, a fiber optic device, and a suction tube are inserted through the incisions. The practitioner cuts away damaged cartilage using the cutting tool while viewing the surgical site through the fiber optic device. The cut cartilage is removed from the body either by grasping the cut cartilage with the cutting tool and removing the cutting tool from the incision, or by using the suction tube to vacuum the cartilage out of the joint area.

A disadvantage of removing the cut cartilage with the cutting tool is that the practitioner needs to remove the cartilage after every cut, thereby inserting and withdrawing the cutting tool many times over. This wastes time, thereby lengthening the duration of the surgical procedure, and also introduces the possibility of causing trauma to the incision and joint each time the cutting tool is inserted and withdrawn. However, if the cartilage is not removed immediately after cutting, it can get lost in the joint and cause damage to the joint.

The practice of removing the cut cartilage via suction is a more desirable practice. Because there is a suction tube close to the surgical site during the entire procedure, the cartilage can be removed virtually immediately after cutting, and before the cartilage is lost in the joint. A disadvantage of using suction is that an extra incision is required for the suction tube. Also, since the suction tube necessarily approaches the surgical site from a different angle than that of the cutting tool it is often difficult to locate the suction tube to remove all of the cut cartilage.

U.S. Pat. No. 4,522,206 to Whipple et al., shows an arthroscopic surgical instrument having an outer tube, an inner tube which is in contact with, extends axially within, and moves within the outer tube, a suction source coupled to the outer tube at a proximal end thereof, a movable upper jaw, and a fixed lower jaw. The movable upper jaw has an upper portion coupled to the inner tube at a flexible extension thereof, and the fixed lower jaw is formed at the distal end of the outer tube. The movable jaw is coupled to the fixed jaw by a pivot pin or stub pins near the lower portion of the outer tube. Axial movement of the inner tube causes the movable jaw to open and close relative to the fixed jaw. The outer tube and inner tube together provide a fluid path from the suction source at the proximal end of the instrument to the jaws at the distal end of the instrument. The provided configuration facilitates suctioning of the cartilage (and fluid) out of the joint area via the jaws and fluid path after the cartilage is cut.

Although the arthoscopic instrument of Whipple et al. appears to solve the problems of the prior art, it still has several disadvantages. A first disadvantage of the Whipple et al. instrument is that the inner tube is coupled to the movable jaw by a flexible portion of the inner tube which is used to close the jaw by pushing the inner tube toward the jaws. This arrangement is incapable of achieving a strong cutting action because the pushing force cannot be arranged to be as great as a pulling force, and because the location of attachment relative to the movable jaw does not provide a large mechanical advantage. A second disadvantage of the Whipple et al. instrument is that the movable jaw is connected to the fixed jaw by means of a pivot pin or stub pins. The pivot or stub pin connection is a common failure point for the instrument because of its weakness. A third disadvantage of the Whipple et al. instrument is that the inner tube which is attached to the movable jaw and is used to actuate the movable jaw, moves axially inside the hollow tube. The axial movement creates friction while opening and closing the upper movable jaw relative to the lower fixed jaw and makes the instrument more difficult to actuate.

Further disadvantages of the Whipple et al. instrument are that the vacuum tube connected to the moving portion of the actuating handle can interfere with the practitioner during the procedure, making it difficult for the practitioner to control the instrument, and that the Whipple et al. instrument is difficult and expensive to manufacture because of the tube design and jaw configuration.

Parent application Ser. No. 07/978,249 describes a preferred jaw assembly which overcomes some of the disadvantages of Whipple et al. In the arrangement of the arthroscopic tool of the parent application, the movable jaw is pivotally attached to the fixed jaw with a tongue and groove configuration. This configuration is more reliable than a configuration which uses a pivot pin. In addition, the closing action is accomplished when a push rod pulls the jaws closed, which permits a higher force to be applied. Construction of the jaw assembly of the parent application, however, requires that the bottom of the fixed jaw be open. As a result, there is no way to provide suction at the distal end of the instrument.

SUMMARY OF THE INVENTION

It is therefore an object of the invention to provide a surgical punch and die arthroscopic instrument having a suction capability.

It is another object of the invention to provide an arthroscopic surgical instrument with a suction capability which has a tongue and groove end effector assembly which is easily assembled.

It is a further object of this invention to provide an arthroscopic surgical instrument with a suction capability which does not require welding of the end effector assembly.

It is an additional object of this invention to provide an arthroscopic surgical instrument having an actuating lever where the source of suction to the arthroscopic instrument does not interfere with the actuating handle.

In accord with these objects, the arthroscopic surgical instrument of the invention broadly includes a surgical punch end effector assembly, a hollow tube defining a fluid passageway, a push rod extending through the hollow tube, an actuating mechanism coupled to a proximal end of the push rod, and a fluid coupler extending into the hollow tube at a proximal portion thereof and coupled to a vacuum source which applies suction through the fluid passageway. The end effector assembly has a movable punch end effector which is coupled to the push rod, and a stationary die end effector. The stationary die end effector includes a separate upper die portion and a separate lower cup portion, both of which are coupled to the distal end of the hollow tube. The upper die and lower cup portions are fixed together at the end of an assembly procedure. The upper die portion of the stationary die end effector has a groove into which a tongue of the movable end effector is fitted prior to fixing the separate portions of the stationary end effector. When the stationary die end effector is assembled with the movable punch end effector rotating therein and the lower cup portion fixed to the upper die portion, and the end effectors are in a closed position, a substantially closed cavity or hollow is formed in the end effectors with the cavity having a proximal opening to the tube formed below the proximal portion of the movable end effector. The cavity is essentially defined on the bottom by the lower cup portion, at the front by the lower cup portion and the upper die portion, and at the top by the movable end effector. With the provided arrangement, when the movable end effector punches tissue into the die, the tissue falls and is held in the cavity. Because the cavity is substantially closed, the suction extends into the cavity and suctions the tissue out through the proximal opening in the cavity, through the fluid passageway, and out of the endoscopic instrument via the fluid coupler.

The actuating mechanism for the push rod preferably includes a fixed handle portion which is coupled to the proximal end of the hollow tube and a movable lever portion which is coupled to the proximal end of the push rod. The movable lever portion pivots relative to the fixed handle portion and imparts a reciprocal axial motion to the push rod which causes the opening and closing of the end effector assembly.

Preferred embodiments of the arthroscopic surgical instrument include: providing the proximal end of the annular passageway with a fluid seal which extends around the push rod; providing the fluid coupler as a socket on the fixed handle portion of the actuating mechanism; and providing the upper die portion and lower cup portion of the stationary die end effector with locking mechanisms so that they attach together as well as attaching to the distal end of the hollow tube without welding.

The objects and advantages of the invention will become apparent to those skilled in the art upon reference to the detailed description taken in conjunction with the provided figures.

Figure 2D:
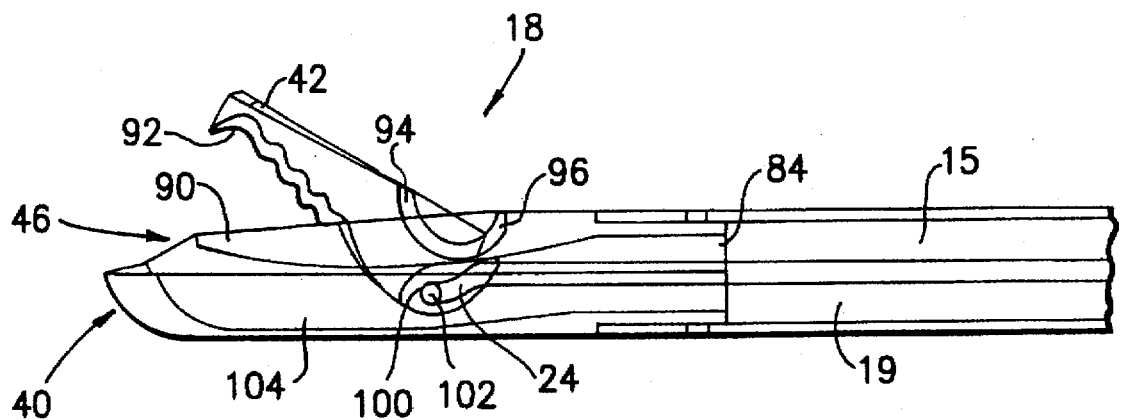
Figure 2E:
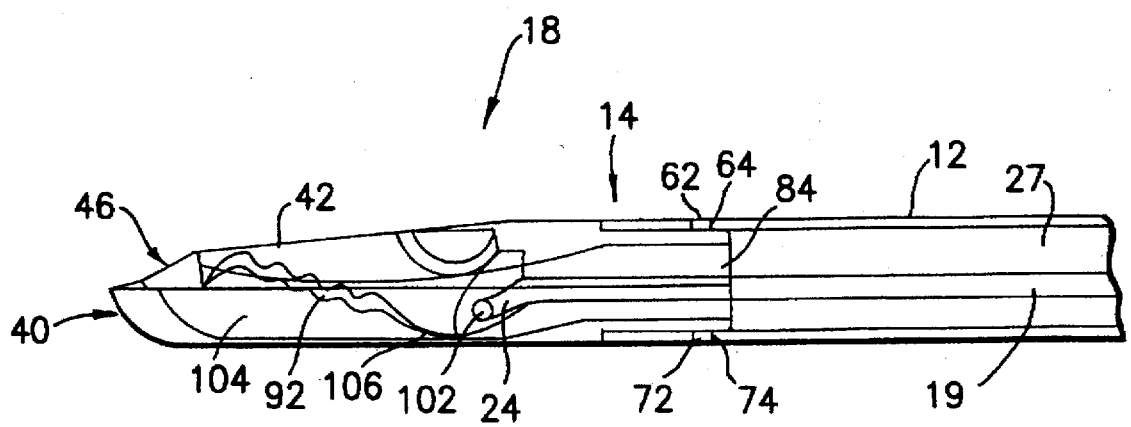
Figure 3:
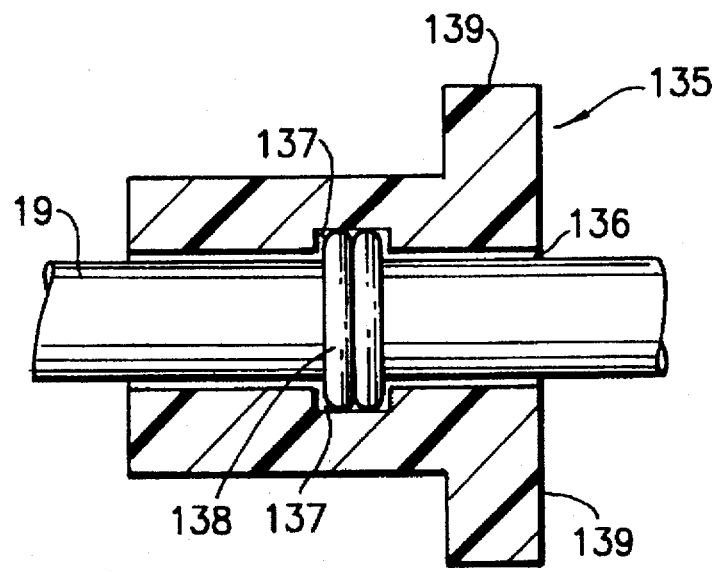

FIG. a 1a is a broken cross-sectional view of the hollow tube showing an annular suction passageway;

FIG. 2 is an enlarged side elevation view in partial section of the end effector assembly in an open position;

FIG. 2a is an enlarged side elevation view in partial section of the end effector assembly in a closed position;

FIG. 2b is an enlarged top view of the end effector assembly in a closed position;

FIG. 2c is a side elevational view of the end effector assembly parts;

FIG. 2d is a transparent side elevational view of the distal end of the hollow tube with the end effector assembly in an open position;

FIG. 2e is a transparent side elevational view of the distal end of the hollow tube with the end effector assembly in a closed position;

FIG. 2f is a perspective view of the shank portion of the end effector assembly;

FIG. 3 is a longitudinal cross-sectional view of the fluid seal; and

Figure 4:
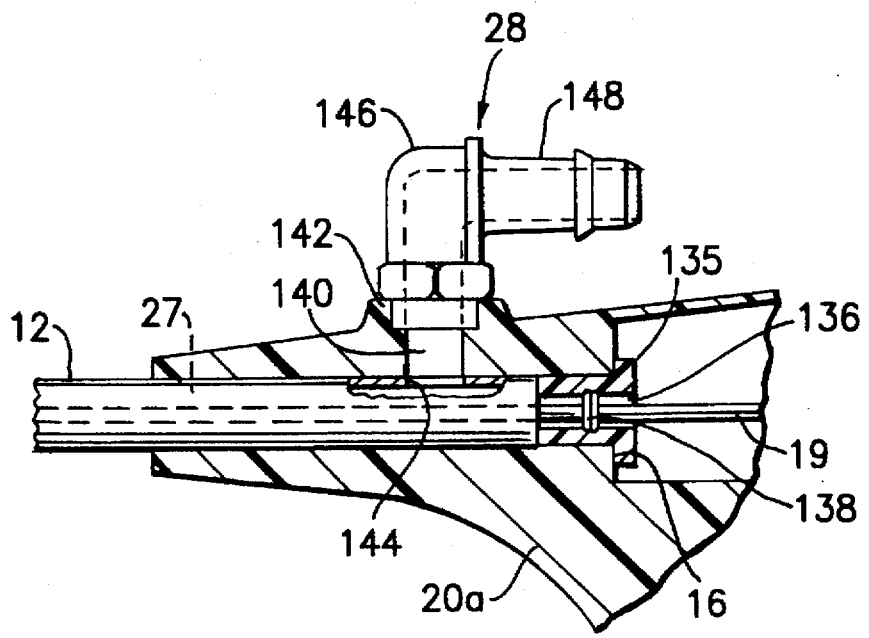

FIG. 4 is a longitudinal cross-sectional view of the suction connector and its connection to the handle portion of the arthroscopic instrument.

DETAILED DESCRIPTION OF THE PREFERRED EMBODIMENT

Figures 1, 1A:
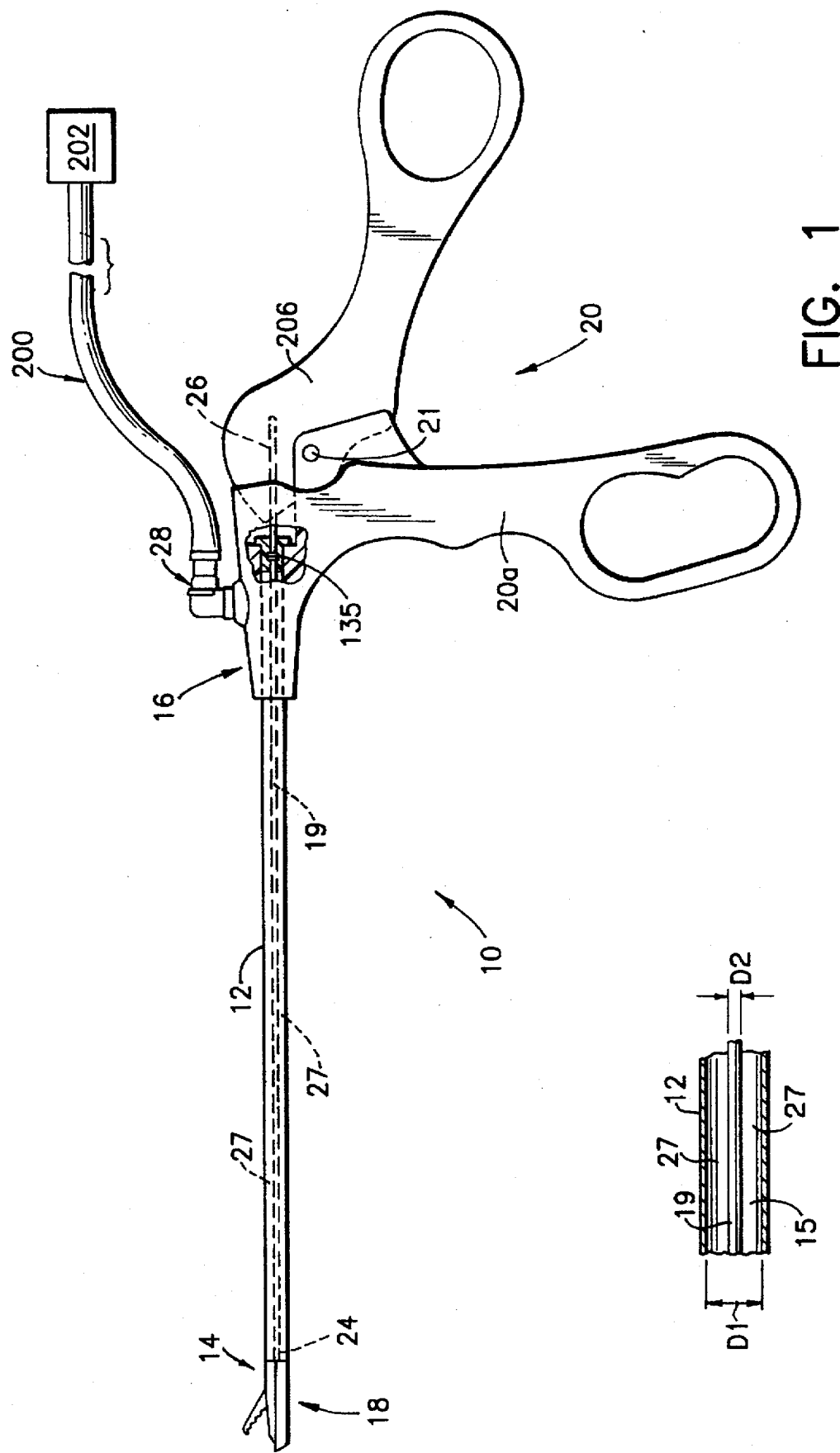
FIG. 1 is a side elevational view in partial section of an arthroscopic surgical instrument according to the invention.

The arthroscopic surgical instrument 10 of the invention is seen in FIG. 1. The arthroscopic instrument 10 includes a hollow tube 12 which has a distal end 14 and a proximal end 16, a surgical punch end effector assembly 18 which is coupled to the distal end 14 of the hollow tube 12, a push rod 19 which extends through the hollow tube 12 and has a distal end 24 coupled to the end effector assembly 18, and an actuating assembly 20 which is coupled to the proximal end 16 of the hollow tube 12 and to the proximal end 26 of the push rod 19. The actuating assembly 20 includes a fixed or stationary handle 20a and a movable lever 20b connected by a pivot pin 21 which permits the lever 20b to pivot relative to the stationary handle 20a. The proximal end 26 of the push rod 19 is coupled to the movable lever 20b of the actuating assembly 20 such that reciprocal axial motion is imparted to the push rod 19 when the movable lever 20b is moved relative to the fixed handle 20a of the actuating assembly 20. The axial motion effects the opening and closing of the end effector assembly 18 as discussed below. As shown in FIG. 1a, an inner diameter D1 of the hollow tube 12 and an outer diameter D2 of the push rod 19 define an annular passageway 27 extending axially through the hollow tube 12. As will be discussed in more detail hereinafter with reference to FIG. 4, the arthroscopic instrument 10 also includes a fluid coupling 28 which is in fluid communication with the annular passageway 27 inside the hollow tube 12.

Details of the surgical punch end effector assembly 18 of the arthroscopic instrument 10 are seen in FIGS. 2–2f. The end effector assembly 18 provides a punch and die cutting arrangement comprised of a stationary die end effector 40 and a movable punch end effector 42. The stationary die end effector 40 is comprised of a separate lower cup portion 44 and a separate upper die portion 46 which interlock as discussed hereinafter to form the stationary die end effector 40. In particular, the lower cup portion 44 of stationary die end effector 40 is generally semicylindrical in shape and includes a bottom surface 44a, side walls 44b, an upwardly curving front surface 44c, a top surface 44d, and a shank portion 44e. Extending from the top surface 44d at the front surface portion 44c in an angled manner is a locking tooth 80. The bottom surface 44a, side walls 44b, and upwardly curving front surface 44c together form a cup which is used to receive cut tissue as discussed in more detail below.

The upper die portion 46 of the stationary die end effector 40 is also generally semicylindrical in shape and includes an upper surface 46a which defines a die cut opening 90, side walls 46b, a downwardly curving front surface 46c, a bottom surface 46d, and a shank portion 46e. Extending from the inner surface 46f of the side walls 46b near the top thereof, are arcuate tongues 96 which extend into grooves 94 of the movable punch end effector 42 described below. Also, formed in the front surface 46c is a locking socket 82. As will be discussed in more detail hereinafter, during assembly of the stationary die end effector 40, the locking tooth 80 of the bottom cup portion 44 is pushed into the locking socket 82 of the upper die portion 46 thereby locking the cup and die portions together with their respective top and bottom surfaces 44d, 46d, and their respective front surfaces 44c, 46c in contact.

The proximal ends of the cup 44 and die 46 portions of the stationary die end effector 40 include the shank portions 44e, 46e. As seen best in FIGS. 2b and 2f, the shank portion 46e of the upper die portion 46 of the stationary die end effector 40 preferably includes two axial cutouts or undercuts 56 dividing the shank portion 46e into two outer segments 58 and one slightly resilient undercut inner segment 60. The undercut segment 60 has a radial outer projection 62 which snaps into a hole or an indentation 64 (see FIGS. 2d and 2e) at the distal end 14 of the hollow tube 12 during assembly as discussed below. It will be noted that the shank portion 44e of the lower cup portion 44 of the stationary die end effector 40 is substantially the same as the shank portion 46e of the upper die portion 46, and preferably has two axial cutouts 66 dividing the shank portion 44e into two outer segments 68 and one slightly resilient undercut inner segment 70. The undercut segment 70 has a radial outer projection 72 which extends into a hole or an indentation 74 at the distal end 14 of the hollow tube 12.

The movable punch 42 of the arthroscopic instrument 10 of the invention is substantially as shown and disclosed in detail in parent application Ser. No. 07/978,249. The movable punch 42 is provided with a top surface 42a, sides 42b, a front surface 42c, and a bottom surface 42d. The top and bottom surfaces 42a, 42d are sized to fit inside the die cut opening 90 of the upper die. The union of the bottom surface 42d and the sides 42b form knife-like edges 92 which provide a cutting and punching action in conjunction with the upper surfaces of the opening 90 of the stationary end effector 40. Formed in an upper area of sides 42b are arcuate grooves 94 into which fit the arcuate tongues 96 of the upper die 46. The movable punch 42 is also provided with a proximal shank portion 98 which is formed with a hole 100. The distal end 24 of the push rod 19 is linked to the movable punch 42 at the hole 100 by a push rod pin 102 (see FIGS. 2d and 2e). Axial movement of the push rod 19 causes the movable punch 42 to pivot relative to the stationary die 40 to an open position such as shown in FIG. 2d or to a closed position as shown in FIG. 2e. The pivoting is obtained as the arcuate grooves 94 in the movable punch 42 ride along the tongues 96 of the stationary die portion of the stationary jaw 40. A more detailed description of the cutting and pivoting action of the movable punch end effector 42 and the upper die portion 46 of the stationary die end effector 40 is found in parent application Ser. No. 07/978,249.

The surgical punch end effector assembly 18 is assembled and connected to the remainder of the arthroscopic surgical instrument 10 in the following manner. With the push rod 19 coupled by push rod pin 102 to the movable punch end effector 42 at hole 100, the movable punch end effector 42 is inserted into the upper die portion 46 of the stationary end effector 40 with the arcuate tongues 94 of the upper die portion 46 mating with the arcuate grooves 96 of the movable punch 42. The lower cup portion 44 is then coupled to the upper die portion 46 to form the stationary end effector 40 by inserting the locking tooth 80 into the locking socket 82 of the upper die portion 46. In so doing, the shank portions 44e and 46e of the lower cup portion 44 and upper die portion 46 surround the push rod 19 and form an annular passageway extension 84. The proximal end 26 of the push rod 19 is then fed through the distal end 14 of the hollow tube 12. As the push rod 19 reaches the proximal end of the hollow tube 12, the shank segments 44e, 46e of the stationary end effector 40 enter the hollow tube 12. Continued movement of the push rod 19 with the end effector assembly 18 causes the outer radial projections 62 and 72 of the shank segments 46e, 44e to enter the hollow tube 12 and to slightly deflect the slightly resilient undercut portions 60, 70 of the shanks. With proper alignment, eventually, the outer radial projections 62 and 72 of the inner segments 60 and 70 of the shank portions 44e, 46e spring into the holes or indentations 64 and 74 at the distal end 14 of the hollow tube 12, thereby coupling the end effector assembly 18 to the hollow tube. This coupling action also serves to further lock the cup 44 and die 46 portions of the stationary end effector 40 together with the respective top and bottom surfaces 44d, 46d, and the respective front surfaces 44c, 46c of the cup and die portions in contact with each other. The proximal end 26 of the push rod 19 then may be coupled to the movable lever portion 20b of the actuating assembly 20 to complete the construction of the arthroscopic instrument 10.

It should be appreciated that with the locking tooth and locking socket mating arrangement, and with the shank portions mating in the distal end 14 of the hollow tube 12, the lower cup portion 44 and the upper die portion 46 mate to form a stationary die end effector 40 without the need for welding the lower cup portion 44 and upper jaw portion 46 together. It will be appreciated that the advantage of this construction is that manufacturing costs are lowered and assembly time is shortened. At the same time, and as will be discussed below, the stationary die end effector so formed provides a substantially closed cavity or hollow 104 which has a proximal opening 106 formed below the proximal portion of the movable punch end effector 42. This cavity is desirable for capturing tissue which is punched by the punch end effector 42, and for permitting the captured tissue to be suctioned out the proximal end of the arthroscopic instrument 10.

As aforementioned, the end effector assembly 18 provides a cavity 104 into which the cut tissue falls after being cut. The cavity 104 is essentially defined by the bottom 44a of the lower cup portion of the stationary end effector 40, the fronts 44c, 46c of the lower cup portion and the upper die portion, and the bottom surface 42d of the movable punch end effector 42. The cavity 104 is connected to the annular passageway 84 defined by the semicylindrical shank portions 44e and 46e of the lower cup and upper die portions of the stationary end effector by the proximal opening 106. The annular passageway 84, in turn, is coupled to, and provides a continuation of the annular passageway 27 in the hollow tube 12.

As shown in FIGS. 1, 3 and 4, the proximal end of annular passageway 27 is defined by a resilient fluid seal or plug 135. The fluid seal 135 has a center bore 136 through which the push rod 19 extends, an inner radial groove 137, a pair of O-rings 138 fitted inside the inner radial groove 137, and a proximal flange 139. The fluid seal 135 is shown fitting frictionally within the proximal end 16 of the hollow tube 12 which is located within the fixed handle portion 20a of the actuating assembly 20. In this manner, and with the flange 139 of the fluid seal 135 abutting the proximal end 16 of the hollow tube 12, the fluid seal 135 blocks and seals the annular passageway 27. As shown in FIG. 4, the push rod 19 extends axially through the hollow tube 12, through the center bore 136 of the fluid seal 135, and through the O-rings 138. The inner radial groove 137 of the fluid seal 135 prevents the O-rings 138 from slipping out of the fluid seal 135 when the push rod 19 is moved axially through the hollow tube 12 and rubs against the O-rings 138. The O-rings 138 thus provide a mechanism for permitting movement of the push rod 19 while preventing leakage out the proximal end of the hollow tube 12. It should be appreciated that by abutting the proximal end 16 of the tube 12, the flange 139 of the fluid seal 135 prevents the fluid seal from slipping completely inside the hollow tube 12. Thus, blockage of the annular suction passageway 27 distal of the fluid coupling 28 is avoided.

The fluid coupling 28, as shown in FIG. 4, is located in a suction bore 140 which is defined by a socket 142 in the fixed handle portion 20a of the actuating mechanism 20. The suction bore 140 is in fluid contact with (i.e., it opens into) the annular passageway 27 in the tube 12 via a radial opening 144 in the tube near its proximal end. The fluid coupling 28, which is known in the art, includes a ninety degree bend 146, and a ridge 148 for receiving and mating with a flexible tubing 200 which in turn couples to a suction source 202. It will be appreciated that with the resilient plug 135 at the end of the tube 12, and with the suction bore 140 and fluid coupling 28 located at the fixed handle portion 20a of the actuating mechanism 20, the suction tube 200 can be kept out of the way of the actuating lever 20b.

The arthroscopic suction instrument 10 of the invention is used during surgery to a joint. Typically, an optical instrument is inserted into the joint at one location, and the arthroscopic suction instrument 10 at another location. A vacuum tube 200 attached to a vacuum source 202 (see FIG. 1) is connected to the fluid coupling 28 of the arthroscopic suction instrument 10. When the practitioner desired to cut tissue in the joint, the practitioner actuates the arthroscopic instrument 10 by opening and closing the handles 20a, 20b, which in turn causes tissue to be punched by the punch and die end effectors 18. The punched tissue falls into the cavity 104 of the end effectors 18. Because the cavity 104 is substantially closed, the suction applied by the vacuum source 202 extends into the cavity 104. Thus, the tissue is suctioned out of the cavity 104 via opening 106, the annular passageway extension 84, the annular passageway 27, radial opening 144, suction bore 140, and out of the endoscopic instrument 10 via the fluid coupler 28. It will be appreciated that if fluid is being used to distend the joint during surgery, the cut tissue will be carried in the fluid. However, because the seal 135 is provided, the fluid will not leak out the handle portion 20 of the instrument.

There has been described and illustrated herein an arthroscopic surgical instrument having suction capability. While particular embodiments of the invention have been described, it is not intended that the invention be limited thereto, as it is intended that the invention be as broad in scope as the art will allow and that the specifications be read likewise. Thus, while particular embodiments of the separate portions of the stationary die end effector were described, it will be appreciated that the separate portions can take different forms. For example, while a locking tooth and locking socket were described on particular portions of the stationary die end effector, it will be appreciated that the tooth and socket could be reversed, and that other or additional locking mechanisms could be used, such as a tongue and groove arrangement on contacting surfaces. Indeed, while not preferred, if desired, the cup portion of the stationary die end effector could be welded to the upper die portion. Also, while a particular arrangement utilizing undercut shank segments with outer radial projections on the shank portions of the stationary die end effector was disclosed for coupling the end effector with the hollow tube, it will be appreciated that other arrangements could be utilized. For example, the projections could be placed on the inside of the hollow tube, and the holes or indentations could be located on the shank segments. It will also be appreciated that while a particular fluid path arrangement was described, other arrangements such as attaching the fluid coupling on the side or bottom of the fixed handle portion of the actuating handle could be utilized. Alternatively, although not preferred, the fluid coupling could be located at the back of the actuating lever of or at other locations. Of course, the fluid seal configuration might change depending upon where the fluid coupling is located. It will therefore be appreciated by those skilled in the art that yet other modifications could be made to the provided invention without deviating from its spirit and scope as so claimed.

We claim:

1. An arthroscopic surgical instrument, comprising:
    a) a hollow tube having a distal end and a proximal end;
    b) an end effector assembly having a longitudinal axis and coupled to said distal end of said hollow tube, wherein said end effector assembly includes a stationary end effector and a movable end effector with pivot means for permitting said movable end effector to rotate relative to said stationary end effector about an axis substantially perpendicular to said longitudinal axis of said end effector assembly, said stationary end effector being cupped and having a bottom inner cup surface, and said movable end effector comprising a punch having a hollowed distal portion, a substantially solid middle portion, and a proximal portion, with a bottom surface of said substantially solid middle portion of said movable end effector and said bottom inner cup surface of said stationary end effector defining a first passageway of sufficient size to receive and pass material punched by said movable end effector;
    c) actuating means extending through said hollow tube and coupled to said proximal portion of said movable end effector, said actuating means for actuating said end effector to open and closed positions, wherein said actuating means and said hollow tube together define an annular second passageway from said distal end of said hollow tube to said proximal end of said hollow tube, said first passageway being in fluid communication with said annular second passageway; and
    d) a suctioning means for applying suction through said annular second passageway and through said first passageway to a space defined by and between said stationary end effector and said movable end effector when said movable end effector is in said closed position, wherein said stationary end effector is comprised of a separate lower cup portion and a separate upper die portion, said upper die portion defining an opening, said separate lower cup and upper die portions being fixed together, said movable end effector punch is sized to fit in said opening of said upper die portion of said stationary end effector, and each of said lower cup portion and said upper die portion has a proximal substantially semicylindrical shank, said shanks coupling to said distal end of said hollow tube.

2. An arthroscopic surgical instrument according to claim 1, wherein:

at least one of said shanks has an outer radial projection, and said hollow tube has at least one radial hole into which said outer radial projection extends.

3. An arthroscopic surgical instrument according to claim 2, wherein:

said shank having said outer radial projection has at least two axial undercuts which define three shank segments, said radial projection being located on a middle of said three shank segments.

4. An arthroscopic surgical instrument according to claim 1, wherein:

said stationary end effector has a die portion with a plurality of walls defining an opening, at least two of said plurality of walls having arcuate tongues, and said movable end effector comprises a punch sized to fit in said opening, said punch having opposed sides each having an arcuate groove, wherein said arcuate tongues fit in said arcuate grooves.

5. An arthroscopic surgical instrument according to claim 1, wherein:

said stationary end effector includes a lower cup portion and an opening, and said movable end effector comprises a punch sized to fit in said opening, wherein when said movable end effector is in a closed position relative to said stationary end effector, a substantially closed cavity is formed in said lower cup portion by said stationary end effector and said movable end effector, said substantially closed cavity having a proximal opening in fluid communication with said annular passageway.

6. An arthroscopic surgical instrument according to claim 1, wherein:

said actuating means includes a push rod, a lever, and a handle, said push rod having a proximal end and a distal end, said distal end of said push rod being coupled to said movable end effector, said lever being coupled to said proximal end of said push rod, said handle being coupled to said proximal end of said hollow tube, and said lever is rotatably coupled to said handle.

7. An arthroscopic surgical instrument according to claim 6, wherein:

said suctioning means includes a first radial hole in said hollow tube and a second radial hole in said handle aligned with said first radial hole.

8. An arthroscopic surgical instrument, comprising:

a) a hollow tube having a distal end and a proximal end;

b) an end effector assembly coupled to said distal end of said hollow tube and being in fluid communication therewith, wherein said end effector assembly includes a stationary end effector and a movable end effector, said stationary end effector having a die portion with a plurality of walls defining an opening, at least two of said plurality of walls having arcuate tongues, and said movable end effector comprising a punch sized to fit in said opening, said punch having opposed sides each having an arcuate groove, wherein said arcuate tongues fit in said arcuate grooves, said stationary end effector having a lower cupped portion with a bottom inner cup surface, and said punch having a hollowed distal portion, a substantially solid middle portion, and a proximal portion, with a bottom surface of said substantially solid middle portion of said movable end effector and said bottom inner cup surface of said stationary end effector defining a first passageway of sufficient size to receive and pass material punched by said punch;

c) actuating means extending through said hollow tube and coupled to said proximal portion of said movable end effector at a location between said arcuate grooves and said bottom inner cup surface, said actuating means for actuating said end effector to open and closed positions, with said actuating means and said hollow tube defining an annular second passageway from said distal end of said hollow tube to said proximal end of said hollow tube, said first passageway being in fluid communication with said annular second passageway; and d) a suctioning means for applying suction through said annular second passageway and through said first passageway to said end effector assembly.

9. An arthroscopic surgical instrument according to claim 8, wherein:

said lower cupped portion of said stationary end effector is fixed to a bottom of said die portion, wherein when said movable end effector is in a closed position relative to said stationary end effector, a substantially closed cavity is formed in said lower cup portion by said stationary end effector and said movable end effector, said substantially closed cavity having said annular second passageway as a proximal opening.

10. An arthroscopic surgical instrument according to claim 8, wherein:

each of said lower cup portion and said upper die portion has a proximal substantially semicylindrical shank, said shanks coupling to said distal end of said hollow tube.

11. An arthroscopic surgical instrument according to claim 10, wherein:

at least one of said shanks has an outer radial projection, and said hollow tube has at least one radial hole into which said outer radial projection extends.

12. An arthroscopic surgical instrument according to claim 11, wherein:

said shank having said outer radial projection has at least two axial undercuts which define three shank segments, said radial projection being located on a middle of said three shank segments.

13. An arthroscopic surgical instrument according to claim 8, wherein:

said actuating means includes a push rod, a lever, and a handle, said push rod having a proximal end and a distal end, said distal end of said push rod being coupled to said movable end effector, said lever being coupled to said proximal end of said push rod, said handle being coupled to said proximal end of said hollow tube, and said lever is rotatably coupled to said handle.

14. An arthroscopic surgical instrument according to claim 13, wherein:

said suctioning means includes a first radial hole in said hollow tube and a second radial hole in said handle aligned with said first radial hole.

15. An arthroscopic surgical instrument, comprising:

a) a hollow tube having a distal end and a proximal end;

b) an end effector assembly coupled to said distal end of said hollow tube, wherein said end effector assembly includes a stationary end effector and a movable end effector, said stationary end effector being comprised of a separate lower cup portion and a separate upper die portion, said upper die portion defining an opening, said separate lower cup portion having a peripheral upwardly directed upper edge and said separate upper die portion having a peripheral downwardly directed lower edge with said upper edge and said lower edge being coextensive throughout substantially their entire length when said lower cup and upper die portions are fixed together, and said movable end effector comprises a punch sized to fit in said opening of said upper die portion of said stationary end effector;

c) actuating means extending through said hollow tube and coupled to said movable end effector, said actuating means for actuating said end effector to open and closed positions; and d) a suctioning means for applying suction through said hollow tube to said end effector assembly.

16. An arthroscopic surgical instrument according to claim 15, wherein:

said upper die portion has a plurality of walls which define said opening, at least two of said plurality of walls having arcuate tongues, and said movable end effector has opposed sides each having an arcuate groove, wherein said arcuate tongues fit in said arcuate grooves.

17. An arthroscopic surgical instrument according to claim 15, wherein:

one of said upper die portion and said lower cup portion has a tooth, and the other of said upper die portion and said lower cup portion has a socket which receives said tooth, said tooth and said socket fixing said upper die and lower cup portions together.

18. An arthroscopic surgical instrument according to claim 15, wherein:

each of said lower cup portion and said upper die portion has a proximal substantially semicylindrical shank, said shanks coupling to said distal end of said hollow tube.

19. An arthroscopic surgical instrument according to claim 18, wherein:

at least one of said shanks has an outer radial projection, said shank having said outer radial projection having at least two axial undercuts which define three shank segments, said radial projection being located on a middle of said three shank segments, and said hollow tube has at least one radial hole into which said outer radial projection extends.

20. An arthroscopic surgical instrument according to claim 15, wherein:

when said movable end effector is in a closed position relative to said stationary end effector, a substantially closed cavity is formed in said lower cup portion by said stationary end effector and said movable end effector, said substantially closed cavity having a proximal opening in fluid communication with said hollow tube.

21. An arthroscopic surgical instrument according to claim 15, wherein:

said actuating means includes a push rod, a lever, and a handle, said push rod having a proximal end and a distal end, said distal end of said push rod being coupled to said movable end effector, said lever being coupled to said proximal end of said push rod, said handle being coupled to said proximal end of said hollow tube, and said lever is rotatably coupled to said handle.

22. An arthroscopic surgical instrument according to claim 21, wherein:

said suctioning means includes a first radial hole in said hollow tube and a second radial hole in said handle aligned with said first radial hole.

\* \* \* \* \*